US00PP11156P

United States Patent [19]

VandenBerg

[11] Patent Number: Plant 11,156

[45] Date of Patent: Dec. 14, 1999

[54] CHRYSANTHEMUM PLANT NAMED 'YOCLARION'

[75] Inventor: Cornelis P. VandenBerg, Salinas, Calif.

[73] Assignee: Yoder Brothers, Inc., Barberton, Ohio

[21] Appl. No.: 09/112,333

[22] Filed: Jul. 9, 1998

[51] Int. Cl.[6] ..... A01H 5/00

[52] U.S. Cl. ..... Plt./286

[58] Field of Search ..... Plt./286, 297

*Primary Examiner*—Howard J. Locker

*Attorney, Agent, or Firm*—C.A. Whealy

[57] ABSTRACT

A distinct cultivar of Chrysanthemum plant named 'Yoclarion', characterized by its compact and uniformly mounded plant habit; freely branching habit; small leaves; uniform and early flowering; numerous and small anemone spray-type inflorescences that are about 3.75 cm in diameter; attractive purple ray florets and purple-tipped disc florets; and good postproduction longevity with inflorescenes and leaves maintaining good substance and color for about three or four weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Yoclarion. The plant is being marketed under the name Clarion.

The new Chrysanthemum is a product of a planned breeding program conducted by the inventor in Salinas, Calif. The objective of the breeding program is to create new pot-type Chrysanthemum cultivars having desirable inflorescence forms and floret colors and excellent post-production longevity.

The new Chrysanthemum originated from a cross made by the breeder in July, 1993, in Salinas, Calif., of two unnamed proprietary Chrysanthemum seedling selections.

The new Chrysanthemum was discovered and selected by the inventor as a flowering plant within the progeny of the stated cross in a controlled environment in Salinas, Calif., in April 1994. The selection of this plant was based on its desirable inflorescence form and floret colors and good postproduction longevity.

Asexual reproduction of the new Chrysanthemum by terminal cuttings harvested in a controlled environment in Salinas, Calif. has shown that the unique features of this new Chrysanthemum are stable and reproduced true to type in successive generations.

SUMMARY OF THE INVENTION

The cultivar Yoclarion has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yoclarion'. These characteristics in combination distinguish 'Yoclarion' as a new and distinct Chrysanthemum:

1. Compact and uniformly mounded plant habit.

2. Freely branching habit, dense plants.

3. Small leaves.

4. Uniform and early flowering.

5. Numerous and small anemone spray-type inflorescences that are about 3.75 cm in diameter.

6. Attractive purple ray florets and purple-tipped disc florets.

7. Good postproduction longevity with inflorescences and leaves maintaining good substance and color for about three or four weeks in an interior environment.

The new Chrysanthemum can be compared to the Chrysanthemum cultivar Regal Desiree (disclosed in U.S. Plant Pat. No. 8,606). However in side-by-side comparisons in Salinas, Calif., and Leamington, Ontario, Canada, under commerical practice, plants of the new Chrysanthemum differed from plants of the cultivar Regal Desiree in the following characteristics:

1. Plants of the new Chrysanthemum have larger inflorescences than plants of the cultivar Regal Desiree.

2. Plants of the new Chrysanthemum have anemone-centered inflorescences whereas plants of the cultivar Regal Desiree have single-type inflorescences.

3. Plants of the new Chrysanthemum flower about two or three days later than plants of the cultivar Regal Desiree.

4. Ray florets of plants of the new Chrysanthemum are lighter in color than ray florets of plants of the cultivar Regal Desiree.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a top perspective view of a typical flowering plant of 'Yoclarion'.

The photograph at the bottom of the first sheet is a close-up view of typical inflorescences of plants of 'Yoclarion'.

The photograph on the second sheet is a close-up view of upper and lower sufaces of typical inflorescences (top) and typical leaves (bottom) of plants of 'Yoclarion'. Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under greenhouse conditions which approximate those generally used in commercial potted Chrysanthemum production. Four unrooted cuttings were directly stuck in a 15-cm container and pinched once. Measurements and numerical values represent averages of typical flowering plants.

Botanical classification: *Dendranthema grandiflora* cultivar Yoclarion.

Commercial classification: Anemone spray-type pot chrysanthemum.

Parentage:

*Male or pollen parent.*—Unnamed proprietary *Dendranthema grandiflora* seedling selection.

*Female or seed parent.*—Unnamed proprietary *Dendranthema grandiflora* seedling selection.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous anemone spray-type pot Chrysanthemum. Inverted triangle. Stems initially upright, then somewhat spreading giving a uniformly mounded appearance to the plant. Freely branching; about four lateral branches develop after removal of terminal apex (pinching), dense and full plants.

*Plant height.*—Compact, about 22 cm.

*Plant width.*—About 33 cm.

*Foliage description.*—Arrangement: Alternate. Length: About 5 cm. Width: About 3.75 cm. Apex: Cuspidate. Base: Attenuate. Margin: Palmately lobed, sinuses between lateral lobes parallel. Texture: Upper and lower surfaces slightly pubescent, very fine white hairs. Veins prominent on lower surface. Petiole length: About 1.5 cm Color: Young foliage upper surface: 147A. Young foliage lower surface: Close to 147B. Mature foliage upper surface: 147A. Mature foliage lower surface: Close to 147B. Venation upper surface: 147A. Venation lower surface: 147B.

Inflorescence description:

*Appearance.*—Anemone spray-type inflorescence form with broadly oblong-shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to about two weeks of long/day short night conditions after planting followed by photoinductive short day/long night conditions flower about eight weeks later.

*Postproduction longevity.*—Inflorescences and leaves will maintain good color and substance for about three or four weeks in an interior environment.

*Quantity of Inflorescences.*—About nine inflorescences per terminal with about 36 inflorescences per plant.

*Inflorescence bud.*—Height: About 6 mm. Diameter: About 7.5 mm. Color: Close to 144A.

*Inflorescence size.*—Diameter: About 3.75 cm. Depth (height): About 1.5 cm. Diameter of disc: About 2 cm.

*Ray florets.*—Shape: Broadly oblong with short corolla tube. Aspect: Straight, flat or slightly concave. Length: About 1.5 cm. Width: About 1.1 cm. Apex: Usually rounded. Margin: Entire. Texture: Smooth, glabrous. Number of ray florets per inflorescence: About 23. Color: When opening, upper surface: 77B. When opening, lower surface: 69A to between about 77C and 77D. Fully opened, upper surface: 77A to 72A to 70A. Fully opened, lower surface: 77C to 77D .

*Disc florets.*—Shape: Enlarged tubular. Apex: Serrated. Length: About 1 cm. Width: Apex: About 2.5 mm. Base: About 1 mm. Number of disc florets per inflorescence: Numerous usually about 110. Color: Immature: 154A. Mature: Apex: 76B to 77D. Midsection and base: Close to 154A. Throat: 77A.

*Peduncle.*—Aspect: Flexible, strong, angled about 50° to stem. Length: First peduncle: About 3.5 cm. Fourth peduncle: About 5.7 cm. Texture: Pubescent. Color: Close to 144A.

*Reproductive organs.*—Androecium: Present on disc florets only. Anther color: 9A. Pollen amount: moderate to low. Pollen color: 9A. Gynoecium: Present on both ray and disc florets.

Disease resistance: No known Chrysanthemum diseases observed to date on plants grown under commerical greenhouse conditions.

Seed production: Seed production has not been observed.

It is claimed:

1. A new and distinct cultivar of Chrysanthemum plant named 'Yoclarion', as illustrated and described.

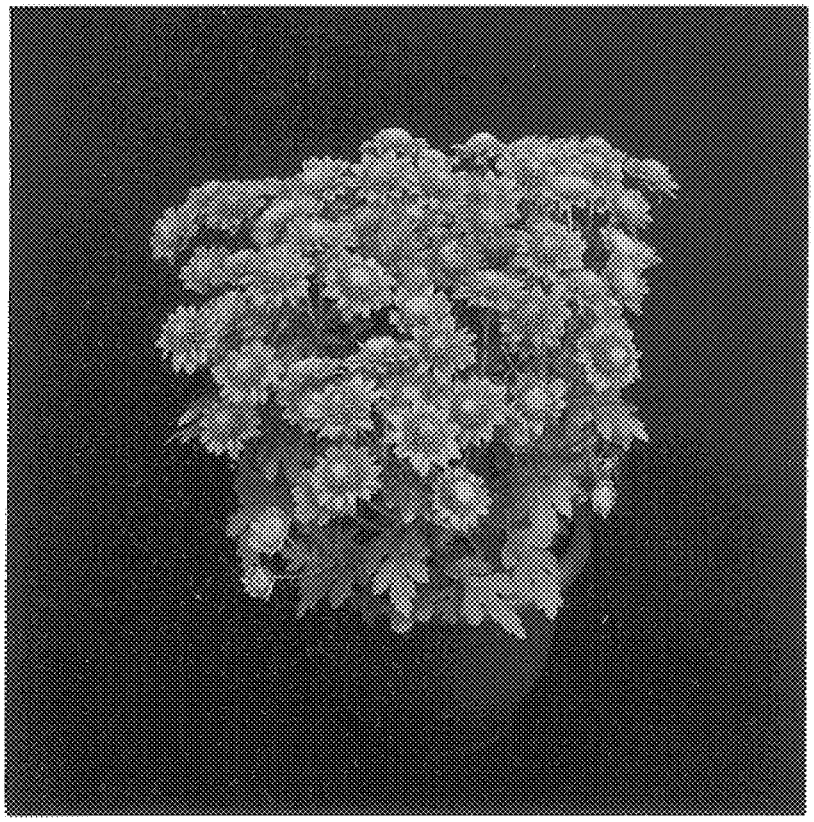
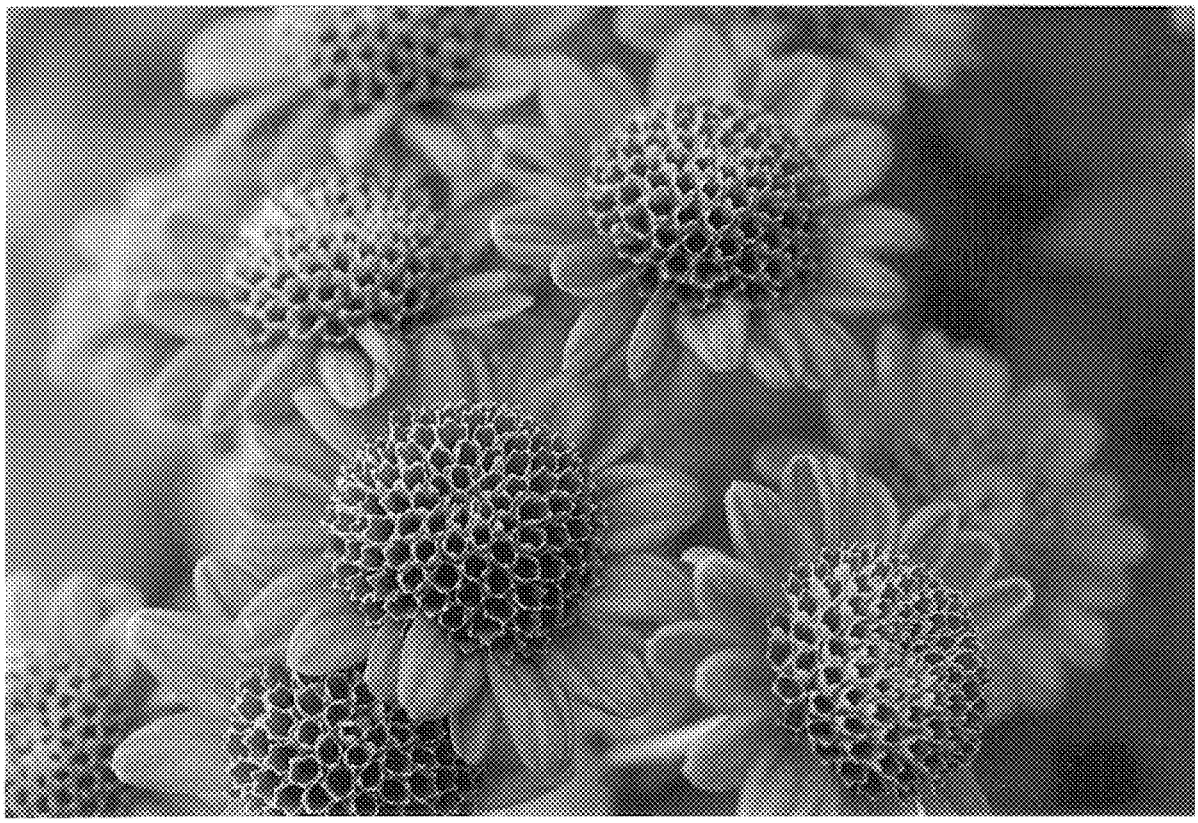

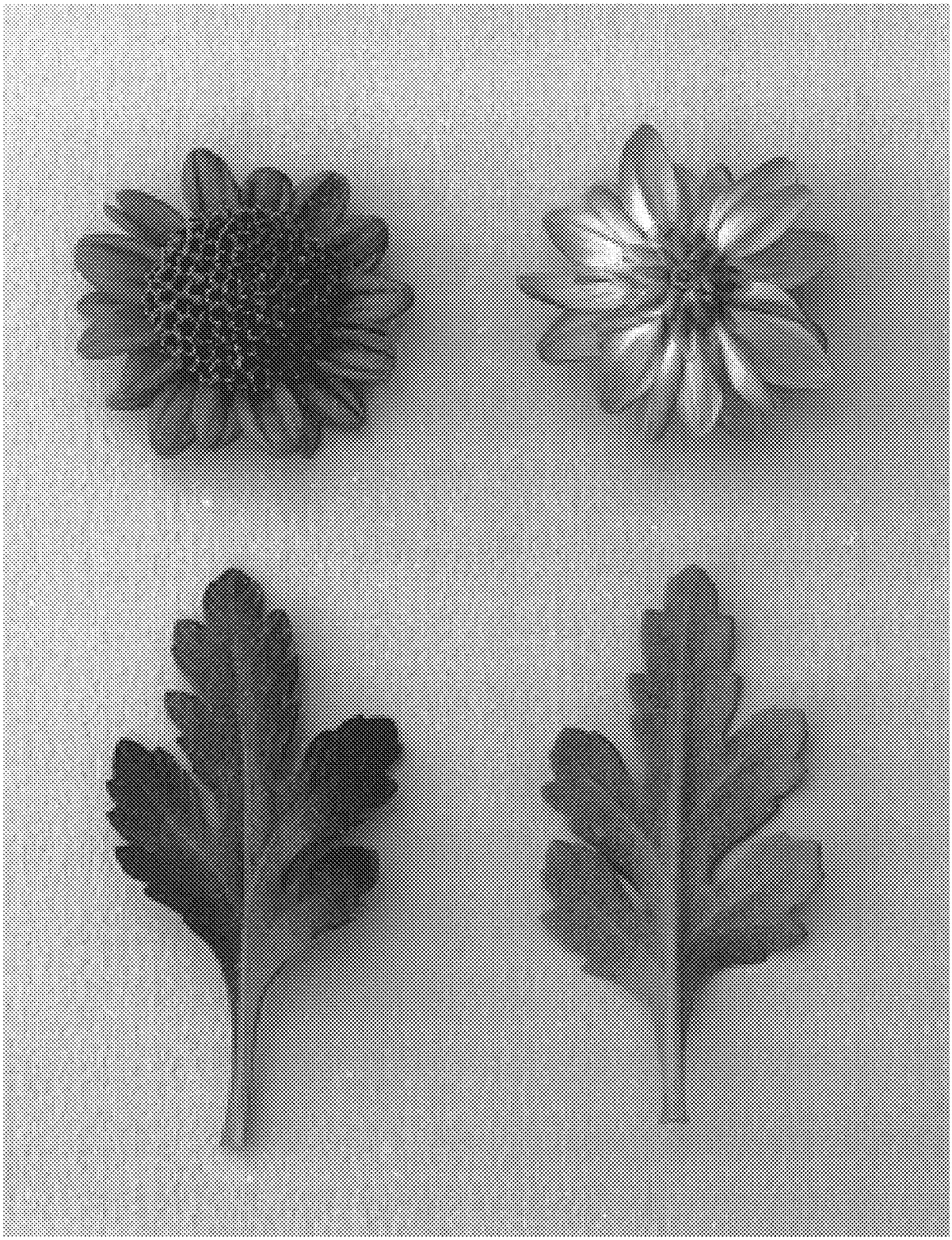

* * * * *